Figure 1:
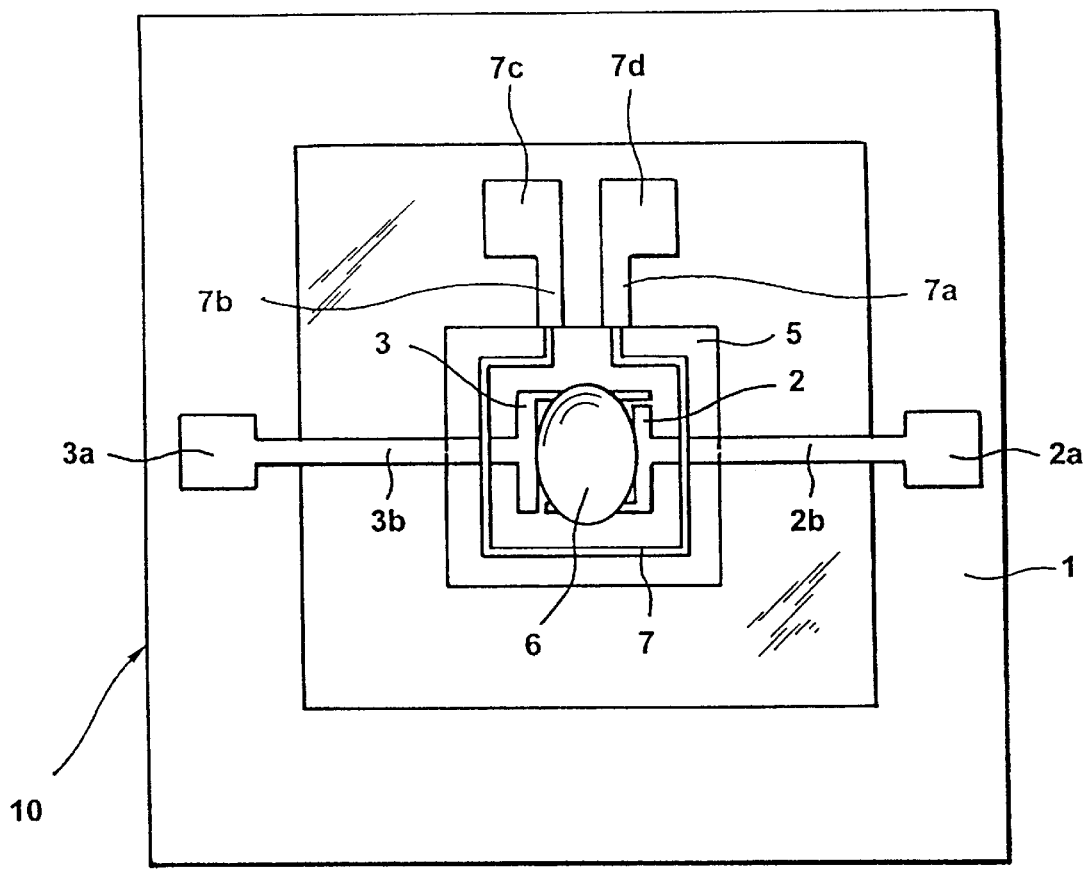

United States Patent [19]
Roth et al.

[11] Patent Number: 6,114,658
[45] Date of Patent: Sep. 5, 2000

[54] DEVICE FOR THE ENCAPSULATED RECEPTION OF A MATERIAL

[75] Inventors: Mathias Roth, Walldorf; Hanns-Erik Endres, München; Hans-Rolf Tränkler, Neubiberg, all of Germany

[73] Assignee: Fraunhofer-Gesellschaft zur Forderung der angewandten Forschung e.V., Munich, Germany

[21] Appl. No.: 09/142,634
[22] PCT Filed: Jan. 28, 1997
[86] PCT No.: PCT/EP97/00373
  § 371 Date: Jan. 4, 1999
  § 102(e) Date: Jan. 4, 1999
[87] PCT Pub. No.: WO97/34697
  PCT Pub. Date: Sep. 25, 1997

[30] Foreign Application Priority Data

Mar. 15, 1996 [DE] Germany ............ 196 10 293

[51] Int. Cl.⁷ ....................................... H05B 1/00
[52] U.S. Cl. .................. 219/209; 338/34; 338/307
[58] Field of Search .................. 219/201, 209, 219/210, 385, 521, 543, 544, 546, 552; 338/306, 307, 308, 309, 34, 35; 73/204.11, 204.16, 204.17, 204.23, 204.25, 204.26; 430/315; 257/253

[56] References Cited

U.S. PATENT DOCUMENTS

| | | |
|---|---|---|
| 4,198,135 | 4/1980 | Erlichman . |
| 4,225,410 | 9/1980 | Pace . |
| 4,706,061 | 11/1987 | Johnson ................. 338/34 |
| 4,772,560 | 9/1988 | Attar . |
| 4,914,742 | 4/1990 | Higashi et al. ............... 73/204.26 |
| 4,928,513 | 5/1990 | Sugihara et al. .............. 338/34 |
| 5,003,812 | 4/1991 | Yagawara et al. ............. 338/34 |
| 5,048,336 | 9/1991 | Sugihara et al. .............. 338/35 |
| 5,262,127 | 11/1993 | Wise . |
| 5,291,781 | 3/1994 | Nagata et al. ................ 73/204.26 |
| 5,345,213 | 9/1994 | Semancik . |
| 5,353,638 | 10/1994 | Marek ......................... 73/204.26 |
| 5,356,756 | 10/1994 | Cavicchi et al. ............. 430/315 |
| 5,406,841 | 4/1995 | Kimura ....................... 73/204.26 |
| 5,464,966 | 11/1995 | Gaitan et al. ................ 219/544 |

FOREIGN PATENT DOCUMENTS

| | | |
|---|---|---|
| 0250948 | 1/1988 | European Pat. Off. . |
| 0316065 | 5/1989 | European Pat. Off. . |
| 0347579 | 12/1989 | European Pat. Off. . |
| 0459239 | 12/1991 | European Pat. Off. . |
| 0471431 | 2/1992 | European Pat. Off. . |
| 3520416 | 12/1986 | Germany . |
| 3818614 | 12/1989 | Germany . |
| 3915920 | 11/1990 | Germany . |
| 3919042 | 12/1990 | Germany . |
| WO 9307463 | 4/1993 | WIPO . |

*Primary Examiner*—Teresa Walberg
*Assistant Examiner*—Fadi H. Dahbour
*Attorney, Agent, or Firm*—Dougherty & Associates

[57] ABSTRACT

An encapsulating device having a material encapsulated therein comprises a basic body provided with a recess for receiving therein the material and formed by microsystem technology in such a way that the material is fully arranged within the recess. A diaphragm extends across the basic body and is implemented in microsystem or thin-film technology. The diaphragm is used for encapsulating the material in the recess of the basic body in such a way that the diaphragm extends in spaced relationship with the material. An electrically actuable heating means is provided for destroying the diaphragm so as to expose the material.

6 Claims, 2 Drawing Sheets

DEVICE FOR THE ENCAPSULATED RECEPTION OF A MATERIAL

The present invention refers to a device for the encapsulated reception of a material, especially a sensitive material. In particular, the present invention deals with a miniaturizable device for the encapsulated reception of a sensitive material, which is adapted to be opened electrically.

In many fields sensitive materials, e.g. chemical indicator materials, catalysts, pharmaceuticals, are used. Sensitive means that the lifetime, i.e. the usability for a specific purpose, is reduced when the material comes into contact with a specific substance or mixture of substances. In view of this limited lifetime, it is desirable to expose these materials only a short time before they are used in the detrimental measurement medium and to keep them under a protective gas or a protective liquid or a vacuum up to this time. The detrimental measurement medium can be identical with the substance to be measured.

Conventional methods used for this purpose are the encapsulation of the substance in a glass bulb, plastic foils or similar packings. These methods are disadvantageous in many respects: the encapsulation methods can be miniaturized only to a limited extent and/or the closure cannot be opened automatically or necessitates complicated measures for being opened automatically. Such sensitive substances are also enclosed in a vessel communicating with the outside world via a valve and/or a hose system. This device can be opened automatically, but the speed with which it is opened mechanically may here be insufficient for some cases of use. It is therefore impossible to react to rapid events. In addition, the necessary mechanics limits the minimum size that can be achieved as well as the reduction of costs.

The direct coating of the substance to be protected e.g. with electrically evaporable materials can-be used only to a very limited extent, since this method often results in an irreversible contamination of the material coated.

DE 3919042 A1 discloses a system for analysing solid substances on mercury. In this known system a solid substance to be analysed is introduced in a vessel which is then closed by a diaphragm; when a cover has been placed on top of the diaphragm onto the rim of the vessel, the diaphragm is destroyed by heating the solid substance and by an excess pressure in the vessel resulting from such heating. The device used in the system disclosed in DE 3919042 A1 is, however, not suitable for large-batch production.

DE 3520416 C2 describes a device for opening a partition in a controlled manner, said partition consisting of a diaphragm inserted in a tightening ring and having heating wires applied thereto, said heating wires causing the diaphragm to open when supplied with electric energy. Also this device is unsuitable for mass production e.g. by means of microchemical methods.

DE 3818614 A1 and DE 3915920 A1 disclose micromechanical structures provided with a plurality of depressions for receiving small amounts of material, in particular in the field of biotechnology. The depressions are closed by means of a cover which is preferably provided with raised portions that are complementary to said depressions.

For the purpose of proving substances in gases or liquids e.g. a plurality of transducers having different structural designs exists. Many of them function according to the principle of measuring the resistance or the capacitance of the indicator material. With regard to such transducer designs reference is made to H.-E. Endres, S. Rost, H. Sandmaier "A PHYSICAL SYSTEM FOR CHEMICAL SENSORS", Proc. Microsystem Technologies, Berlin, 29.10.-01.11.91, 70–75. A change in this quantity (these quantities) is correlated with an event in the medium to be examined. The structures, e.g. interdigital structures, required for measuring e.g. the resistance are often applied to a substrate in thin-film technology, said substrate being e.g. silicon, quartz. The support of these sensors can itself again be a diaphragm structure.

The production of thin diaphragm structures, e.g. $Si_3N_4$ on an Si support material and other combinations, has been known from the field of microsystem technology for many years. Normally, these diaphragm structures are used because of their very low heat capacity and/or heat conductivity. They serve as a support material for temperature-sensitive resistors, e.g. for realizing a thermal flowmeter and/or for thermally insulating a heating element from its surroundings.

It is therefore the object of the present invention to provide a device for the encapsulated reception of a material which prevents contamination of said material and which can be opened rapidly an easily.

This object is achieved by a device according to claim 1.

The present invention provides a device for the encapsulated reception of a material, comprising a basic body formed by microsystem technology and provided with a recess for receiving therein the material, a diaphragm extending across said basic body and implemented in microsystem or thin-film technology, said diaphragm being used for encapsulating the material in said recess of the basic body, and an electrically actuable heating means for destroying said diaphragm so as to expose the material.

Due to the fact that the sensitive material is separated from the surroundings by the diaphragm, the structure according to the present invention offers the possibility of rapidly exposing the material in a simple and contamination-proof manner, the structure being easily producible by large-batch production. By means of a suitable electrode geometry it can be signalized that the encapsulation has been duly opened.

In other words, the present invention makes use of a structure which is adapted to be implemented by well-known, large-batch production methods. For this purpose, a diaphragm/basic-body structure implemented in microsystem technology will be particularly suitable for encapsulating the sensitive material. The diaphragm can, however, also be implemented in thin-film technology for the purpose of the present invention.

Hence, the present invention provides a device by means of which sensitive layers or materials can be shielded from their surroundings at a very reasonable price; if necessary, this encapsulation can be released easily.

According to an essential effect of the present invention, the invention makes use of the fact that high stresses often occur in thin diaphragms implemented in thin-film technology or microsystem technology, such stresses being, in other fields of technology, regarded as a problem entailed by such diaphragm structures. These stresses existing in the diaphragm cause said diaphragm to burst explosively when thermal forces are applied thereto.

Since the diaphragm does, in this case, not evaporate but shatter into individual pieces, the sensitive material or the layer of sensitive material will be contaminated by diaphragm fragments only to a minor degree, which can be neglected in most cases of use, said diaphragm fragments being chemically comparatively inert when a suitable material is chosen for the diaphragm.

Even this kind of deposition of diaphragm fragments can be excluded in the case of the structure according to the present invention by introducing a protective gas under slight excess pressure or by placing the diaphragm opening in the direction of the gravitational force.

The heating means of the device according to the present invention is preferably implemented as a heater integrated on the diaphragm. In the case of this embodiment, a short heating pulse causes a thermal strain in the diaphragm by means of which said diaphragm is caused to burst. The time required for such opening will be much shorter than one second, typically it will be in the millisecond region. Hence, the present invention provides an economy-priced and microsystem-compatible device for encapsulating sensitive materials, which permits simple and rapid opening of the encapsulation, prevents a contamination of sensitive materials and is also suitable for series production.

According to a more far-reaching aspect of the present invention, the layer-encapsulating device according to the present invention defines a constituent part of a sensor component having arranged thereon the sensitive material in the form of an indicator material. By causing the diaphragm to burst, such a sensor can automatically be activated for measurements at any time.

Figure 2:
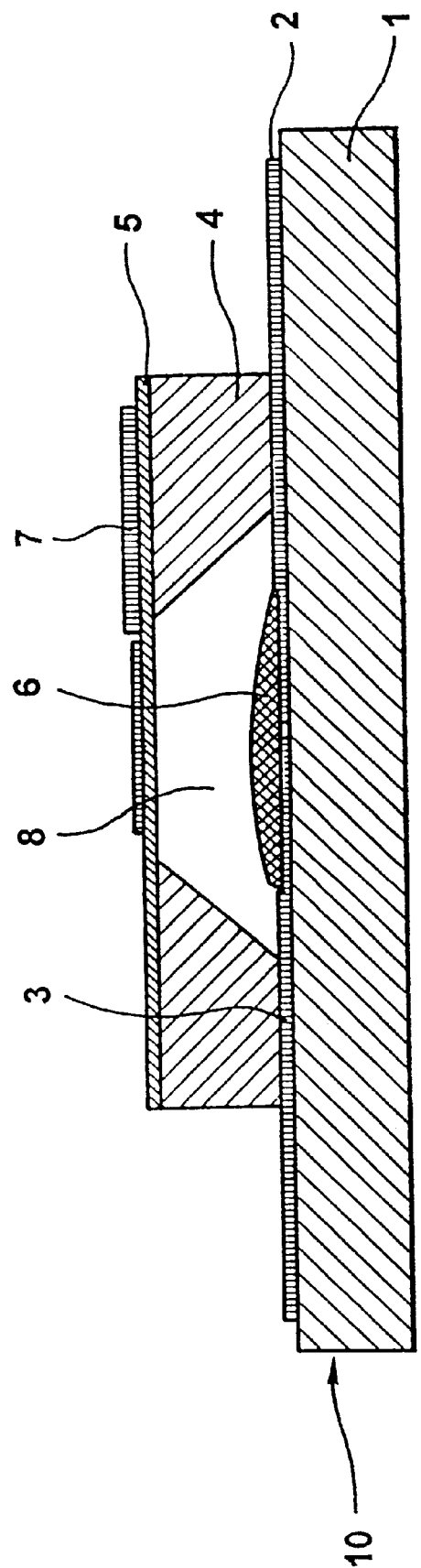

In the following, preferred embodiments of the present invention will be explained in detail making reference to the drawings enclosed, in which:

FIGS. 1 and 2 show a top view and a cross-sectional view of a gas sensor component.

A gas sensor component, indicated generally by reference numeral 10 in FIGS. 1 and 2, comprises a support 1 consisting e.g. of quartz and having applied thereto the measuring elements (e.g. conducting track structures, MOSFET, SAW etc.) 2, 3 of an interdigital structure for capacitance and/or resistance measurement with the associated connecting lines 2b, 3b and connection areas 2a, 3a. The interdigital structure is covered with an indicator material 6. In the embodiment of the gas sensor component 10 shown in the present connection the indicator material is 3-aminopropyl trimethyloxysilane, which, on exposure to air, only has a limited lifetime of three months. Hence, it is desirable that the layer of indicator material is only brought into contact with the ambient air a short time before it is used so that the whole lifetime of the layer of indicator material can be utilized.

For the purpose of encapsulation, the support 1 is provided with a diaphragm holding structure 4 on the side having provided thereon the indicator material 6; in the embodiment shown in the present connection, said diaphragm holding structure consists of a silicon wafer in which the recess 8 has been provided by conventional photolithographic and etching methods. A person skilled in the art working in the field of microsystem technology will know without further explanation that methods for producing a diaphragm extending across a holding structure are nothing out of the common in the field of microsystem technology and that said methods normally comprise the steps of applying a diaphragm 5 first to a holding structure 4 and forming then the recess 8 in said holding structure 4 by photolithographic and etching methods.

Although the diaphragm 5 may also consist of silicon, other materials, such as a plastic foil and glass, may be used as well.

A heating structure 7, which is connected to connection areas or bond pads 7c, 7d via connecting lines 7a, 7b, is provided on the diaphragm.

When it is desired to bring the layer of indicator material 6 of such a gas sensor component 10 into contact with the ambient air so that said gas sensor component can be used, the diaphragm 5 will automatically be destroyed after insertion of said gas sensor component 10 into a measuring instrument and a short time before the measurement is started; the diaphragm 5 is destroyed by supplying a current impulse to the heater 7, said current impulse causing the already described destruction of the diaphragm 5. This has the effect that the sensitive layer of indicator material 6 is put into service.

Deviating from the above-described individual sensor, the device according to the present invention is also suitable for encapsulating a plurality of sensors e.g. on a chip, which are operated in cascade in a gas metering unit. When a gas sensor component is exhausted because its layer of indicator material 6 has reached the end of its lifetime, a suitable control electronics will automatically activate a further gas sensor component for use in the measurement process by destroying the diaphragm of said gas sensor component. In this way, the maintenance-free operating time of a gas metering unit will be multiplied.

Another example where the device according to the present invention can be used for encapsulating sensitive layers is the encapsulation of irreversibly operating indicator materials.

This class of materials carries out an irreversible detection reaction with the substance to be detected so that a sensor can only carry out one measurement. The advantage of these materials resides in their simpler chemistry for carrying out a specific (chemical) detection. The number of irreversible recognition reactions known from the literature is much higher than the number of known reversible recognition reactions. In most cases this also entails a higher selectivity (e.g. immuno-reaction). There are also many cases where calibration is not necessary. The transducer can be provided within the encapsulation or outside (=a transducer for all encapsulated layers) the same.

The device described in the present connection permits a comparatively uncomplicated structural design of a large array of single-use sensors, each sensor being encapsulated according to the method described. This encapsulation can be carried out simultaneously for the whole array. For this purpose, the component provided with the diaphragm must be placed onto the support coated with the indicator. Due to the high miniaturization possibilities offered by the present method, the size of the whole array can be kept very small.

It is also possible to arrange the heater in the recess 8 so that a thermally produced excess pressure of a gas filling in said recess 8 can be used for blasting off the diaphragm.

What is claimed is:

1. An encapsulating device having a material encapsulated therein, said encapsulating device comprising the following features:

a basic body formed by microsystem technology and provided with a recess for receiving therein the material in such a way that the whole material is arranged within said recess in spaced relationship with the face of the basic body in which an opening of said recess is formed;

a diaphragm implemented in microsystem or thin-film technology and extending across said basic body and said opening of said recess such that the material is encapsulated in said recess of the basic body in such a way that the diaphragm extends in spaced relationship with said material; and a electrically actuable heating means for destroying said diaphragm so as to expose the material.

2. A device according to claim 1, wherein said basic body (1, 4) comprises a sensor component (1, 2, 3) on which the material is arranged in the form of an indicator material.

3. A device according to claim 2, wherein the sensor component comprises a support material (1, 2), a sensor structure (2, 3) and a layer of indicator material (6) covering said sensor structure at least partially.

4. A device according to claim 2 or 3, wherein said basic body (1, 4) includes a diaphragm support structure (4) which encloses the sensitive area of the sensor component (2, 3) covered with said indicator material (6) and which supports the diaphragm (5) on the side facing away from the sensor component (2, 3).

5. A device according to one of the claims 2 to 4, wherein the sensor component (1–3) and the indicator material (6) form together a gas sensor.

6. A sensor array comprising a plurality of devices according to one of the claims 2 to 5, which are formed on a common support material (1).

* * * * *